(12) United States Patent
Lindner

(10) Patent No.: US 8,054,459 B2
(45) Date of Patent: Nov. 8, 2011

(54) INSPECTION SYSTEM AND METHOD

(75) Inventor: Richard Lindner, Warren, NJ (US)

(73) Assignee: Envirosight LLC, Randolph, NJ (US)

( * ) Notice: Subject to any disclaimer, the term of this patent is extended or adjusted under 35 U.S.C. 154(b) by 115 days.

(21) Appl. No.: 12/357,273

(22) Filed: Jan. 21, 2009

(65) Prior Publication Data

US 2009/0180110 A1    Jul. 16, 2009

Related U.S. Application Data

(63) Continuation-in-part of application No. 11/368,902, filed on Mar. 6, 2006, now Pat. No. 7,480,041, which is a continuation of application No. 10/369,330, filed on Feb. 19, 2003, now Pat. No. 7,009,698, said application No. 10/369,330 is a continuation of application No. 09/564,953, filed on May 4, 2000, now Pat. No. 6,538,732.

(60) Provisional application No. 60/726,918, filed on Oct. 14, 2005, provisional application No. 60/132,400, filed on May 4, 1999.

(51) Int. Cl.
*G01N 21/00* (2006.01)

(52) U.S. Cl. ..................... 356/241.1

(58) Field of Classification Search ..... 356/241.1–241.2
See application file for complete search history.

(56) References Cited

U.S. PATENT DOCUMENTS

| | | | |
|---|---|---|---|
| 3,730,632 A | 5/1973 | Chikama | |
| 4,115,804 A | 9/1978 | Morton et al. | |
| 4,158,490 A | 6/1979 | Gottschalk et al. | |
| 4,246,604 A | 1/1981 | Hundertmark et al. | |
| 4,917,488 A | 4/1990 | Glass | |
| 4,980,763 A | 12/1990 | Lia | |
| 5,065,249 A | 11/1991 | Horn et al. | |
| 5,070,401 A * | 12/1991 | Salvati et al. | 348/141 |
| 5,115,136 A | 5/1992 | Tomasch | |
| 5,134,471 A | 7/1992 | Gendron et al. | |
| 5,193,405 A | 3/1993 | Oomichi et al. | |
| 5,205,174 A | 4/1993 | Silverman et al. | |
| 5,305,356 A | 4/1994 | Brooks et al. | |
| 5,552,822 A | 9/1996 | Nallakrishnan | |
| 5,577,130 A | 11/1996 | Wu | |

(Continued)

FOREIGN PATENT DOCUMENTS

EP    1051037    8/2000

(Continued)

OTHER PUBLICATIONS

Prior Art Statement of Stephen J. Driscoll; portion of blue print dated prior to Oct. 14, 2004.

"Drop-In-Camera Helps Prioritize Sewer Repairs," WaterWorld, p. 84 (May 1998).

*Primary Examiner* — Michael P Stafira
(74) *Attorney, Agent, or Firm* — Saul Ewing LLP

(57) ABSTRACT

A method of inspecting a lateral pipe extending from a manhole, said method comprising: (a) inserting an imaging head into said manhole using a positioning system, said imaging head connected to an elongated member and comprising an imaging device adapted to convert an image to an image signal, a lens optically coupled to said imaging device, and at least one lamp suitable for projecting a light beam, said lamp having a beam that is adjustable to enable said beam to move relative said imaging device; (b) imaging a target located within said lateral pipe; (c) holding said imaging device essentially steady while imaging said target and adjusting said beam to adjust the illumination of said target.

24 Claims, 9 Drawing Sheets

U.S. PATENT DOCUMENTS

| | | |
|---|---|---|
| 5,712,677 A | 1/1998 | Fraering, Jr. et al. |
| 5,867,217 A | 2/1999 | Okino et al. |
| 6,029,918 A | 2/2000 | Sundberg |
| 6,088,612 A | 7/2000 | Blair |
| 6,101,408 A | 8/2000 | Craine et al. |
| 6,293,676 B1 | 9/2001 | Holway |
| 6,313,869 B1 * | 11/2001 | Hyp et al. .................... 348/84 |
| 6,431,270 B1 | 8/2002 | Angle |
| 6,538,732 B1 | 3/2003 | Drost et al. |
| 6,955,100 B1 | 10/2005 | Barich et al. |
| 7,009,698 B2 | 3/2006 | Drost et al. |
| 2004/0021858 A1 | 2/2004 | Shima et al. |
| 2004/0183899 A1 | 9/2004 | Shiota |

FOREIGN PATENT DOCUMENTS

| | | |
|---|---|---|
| FR | 270515 | 11/1994 |
| WO | 2007047338 | 4/2007 |

* cited by examiner

INSPECTION SYSTEM AND METHOD

REFERENCE TO RELATED APPLICATIONS

This application claims priority to U.S. Provisional Patent Application No. 60/726,918 filed Oct. 14, 2005, U.S. application Ser. No. 11/368,902, now U.S. Pat. No. 7,480,041, and all of which are hereby incorporated by reference.

FIELD OF INVENTION

The present invention relates generally to the inspection of areas that are hard-to-reach, inaccessible or uninhabitable for humans. More specifically, the invention relates to the inspection of manholes and lateral pipes radiating therefrom prior to invasive procedures such as cleaning and comprehensive exploratory inspections.

BACKGROUND OF THE INVENTION

It is often necessary to inspect and maintain areas under conditions that render them inaccessible or otherwise uninhabitable for humans for an extended period. These conditions include, for example, small confined spaces and harsh environments such as insufficient air/oxygen, presence of toxins, radioactivity, contamination, excessive dust, dirt and filth, and high noise levels. These conditions can be found, for example, in areas common to storm and sewer pipes, nuclear reactors and containment structures, fossil fuel plants and petrochemical refining facilities just to name a few. Although each area presents its own problems and complexities with respect to inspecting and maintaining, the inconvenient and time-consuming nature of performing an initial inspection is common to all.

For illustrative purposes, the inspection of storm and sewer pipes is considered in detail, although the scope of the present invention is by no means limited to this application. Most municipalities contain a vast network of storm and sewer pipes, often representing the oldest infrastructure in the community.

Periodically, these pipes must be inspected for problems such as cracks, blockage, build-up, and root infiltration. To this end, it is common for an invasive device such as a pipe crawler or push camera to be introduced into the pipe to perform the inspection. Although effective in obtaining detailed images, using a pipe crawler is inconvenient and requires a great deal of time to set up and operate even if no problem is discovered. Furthermore, the use of pipe crawlers is frequently limited by the size and configuration of pipes to be entered. In this regard, often the condition of the pipe (e.g., debris and fractures) prevents the use of invasive inspection devices like crawlers. Therefore, there is a need for a more convenient approach to inspect and maintain underground pipes without the time and complexity associated with invasive techniques such as the use of pipe crawlers or push cameras.

Recently, this need has been fulfilled by the QuickView® inspection device commercially available from Envirosight and described in U.S. Pat. No. 6,538,732 and U.S. application Ser. No. 10/369,330, upon which the present application is based. The QuickView® inspection device provides for a quick and convenient non-invasive approach to ascertain the condition of an inaccessible or uninhabitable area before initiating an invasive procedure such as a comprehensive inspection or cleaning. More specifically, rather than physically entering the area with a robotic or push camera, a highly-maneuverable, hand-held inspection system is provided having an imaging head which can be readily positioned to image the general area initially, and then to zoom in on a target to obtain its image with the desired degree of detail. Thus, the device obtains images of inaccessible or uninhabitable areas by maneuvering an imaging head and using its magnification capabilities, rather than by physically entering the area.

Once the images are obtained, an analysis may be performed to determine whether problems such as cracks, blockage, and root infiltration exist. The images obtained in one embodiment are in a readily-transmittable form, such as a bitmap, thereby allowing them to be transmitted off-site for analysis if desired. If no problem is detected, then the device can be moved quickly to another area to perform another inspection. This way, the time of setting up and operating a pipe crawler or similar device is not wasted on areas that are in acceptable condition.

On the other hand, if a problem is detected, an invasive procedure may be performed to correct or further assess the problem. For example, if a crack is detected, a more comprehensive inspection may be performed in which an invasive inspection device, such as a pipe crawler or push camera, is introduced in the pipe to obtain detailed images pursuant to formulating a plan to remedy the situation. Likewise, if the initial inspection detects that a pipe is clogged, it may be cleaned contemporaneously by introducing an invasive cleaning device into the pipe to remove the obstruction. Thus, rather than awkwardly halting cleaning operations between invasive inspections, a blockage situation may be quickly and easily ascertained on the spot, in one embodiment while the cleaning personnel standby.

Although the QuickView® inspection device has been effective in performing non-invasive inspecting and maintenance, there is an ongoing need to improve the performance and maneuverability of the inspection device. In particular, applicant recognizes a need to improve the device's ability to focus on a target at long range down a pipe. The present invention fulfills this need among others.

SUMMARY OF INVENTION

The present invention provides a system and method for improving inspection of lateral pipes by enabling the imaging head to focus on a target at longer range down a pipe than previously possible. In one respect, Applicants recognize that the performance of the inspection system can be improved dramatically if the imaging head is positioned reliably in an optimum location with respect to the lateral pipe. This position is referred to herein as the "sweet spot." Generally, the optimum position is where the illumination source or lamp is positioned such that its light beam propagates down the pipe to the furthest extent possible before reflecting off the pipe wall and diffusing. Since a target must be well illuminated for effective imaging, the further light is able to propagate down the pipe, the greater the imaging range will be. If the pipe is essentially free of material, the sweet spot will be approximately in the center of the pipe. If, however, the pipe is partially filled with material, particularly liquids, which tend to reflect light, then the sweet spot will be approximately in the center point of the space above the material.

Applicants have identified several features an imaging system that enhance its positioning in the sweet spot or otherwise improve its performance. For example, the system may have calibration capability to position the imaging head at a certain predetermined vertical position based on the expected diameter of the pipe prior to inserting the imaging head down the manhole. By way of contrast, the vertical position of the imaging head cannot be adjusted to fall within the sweet spot using a traditional pan and tilt mechanism after the imaging head is inserted in the manhole. That is, if the vertical position of the imaging head is above or below the sweet spot initially, tilting the head will not rectify the situation, but rather cause the light beam to be angled relative to the pipe. Once the light beam is angled relative to the pipe, its incidence with the pipe wall is shortened, thereby resulting in a rapid diffusion of light. Therefore, it is critical that the imaging head be positioned in the precise vertical location of the sweet spot. Applicants have found that this may be accomplished by calibrating the system to be offset a certain distance from the bottom of the pipe. Using the bottom of the pipe as the reference surface is preferred since the distance from the center to the bottom of the pipe tends to be more predictable than the distance from the center to the top of the pipe.

Furthermore, the system is preferably adjustable in situ. Applicants appreciate that often the user does not know the state or condition of the pipe prior to inspection (i.e., whether it contains material/debris). Therefore, to position the imaging head in the sweet spot, some degree of adjustability is required. The imaging head is, in one embodiment, adjustable in situ to eliminate the need to withdraw the imaging head from the pipe for each adjustment.

Additionally, Applicant recognizes that, once the imaging head is positioned in the sweet spot, its position should be held stable for effective imaging. Imaging at relatively long range using high magnification requires the head to remain very still, otherwise the target images will be blurry.

Yet another feature that facilitates long-range imaging is an adjustable light beam. That is, applicant recognizes that once a target is imaged down a pipe, slight adjustment of the lamp(s) while holding the imaged target steady can significantly improve the illumination of the target, and thus the quality of the image. Applicant has identified a number of applications in which such an adjustment is beneficial. For example, it is often necessary to tilt the imaging head upwardly or downwardly for longer-range imaging of inclining and declining pipes, respectively. Applicant has observed, however, that tilting the imaging head a sufficient degree to image down an inclining or declining pipe will generally result in the light beam overshooting the sweet spot, causing the beam to reflect off the top or bottom of the pipe wall, respectively. Therefore, to position a light beam back in the sweet spot after the imaging head is tilted, the beam needs to be separately adjustable from the imaging device.

Another need for a separately adjustable light beam is to reconcile the size difference between the field of view of the image device and the light beam. By way of background, higher quality images are generally obtained by keeping the field of view as broad as possible. This results in a field of view that tends to be significantly broader compared to a beam of light. Accordingly, having the ability to adjust the beam within the field of view enables enhanced imaging of a target within the field of view. Still another reason to adjust the beam is to exploit certain environmental situations such as water or obstructions, which may affect the way the beam propagates down a pipe. By adjusting the beam, these environmental factors may be avoided/exploited to enhance the image of the target. Yet another reason to adjust the beam is to move it closer to the optical axis of the imaging device as the magnification level increases. In other words, as the magnification level increases and the field of view becomes smaller, the beam should converge on the optical axis such that it remains in the field of view.

Still another desirable feature of an inspection device suitable for long-range imaging down a pipe is to have the optical axis of the image device closely align with the axis of the beam of the lamp. Specifically, having the light beam essentially coincident with the optical axis is one way to maximize the illumination of the field of view. Although this may be performed, in one embodiment, by adjusting the beam as mentioned above, it is generally desirable to have the lamp and imaging device aligned initially.

Thus, for optimum performance for imaging down the pipe, the imaging head should have features that provide calibration, alignment, adjustability, and stability. These are often opposing design objectives.

The imaging head of the present invention satisfies one or more of these opposing design objectives by employing, in one embodiment, a targeting fixture to provide moderate resilient force as a user urges the imaging head into the sweet spot. The targeting fixture comprises, in one embodiment, a resilient member extending from the imaging head. In use, the inspection device is lowered into a manhole (or similar structure) until the targeting fixture rests on the bottom of a pipe (or similar structure). The user then pushes down on the imaging device until the imaging head is in the sweet spot. It has been found that pushing against the resilient targeting fixture provides a high degree of stability-essential during high magnification. Thus, the targeting fixture of the present invention enables the imaging head to be positioned in the sweet spot to achieve maximum illumination down the pipe, while providing enhanced stability for focusing on targets further down the pipe than previously possible.

In another embodiment, the present invention facilitates imaging an object at a relatively long distance by providing an imaging head having at least one lamp having an adjustable beam to enable the beam to move relative to the imaging device.

In yet another embodiment, the present invention facilitates imaging an object at a relatively long distance by aligning the lamp and imaging device. To this end, in certain embodiments, it is desirable to register both the lamp and the imaging head to the enclosure of the imaging head. In other words, if the lamp and the imaging device are both aligned with respect to the enclosure of the imaging device, then the two components will also be alignment. One way to achieve this alignment is to secure the imaging device snugly in the enclosure such that the position of its lens is essentially "locked" in place in the enclosure.

In sum, the present invention involves recognizing the sweet spot in pipe inspection, identifying design objectives for operating in the sweet spot, providing a solution meeting the design objectives, and synergistically combining other technologies with the solution to provide an inspection system offering enhanced imaging of and data gathering from a target in a pipe at a range longer than conventional inspection devices can provide.

Accordingly, one aspect of the invention is a method of inspecting a pipe by positioning the illumination source in the sweet spot for enhanced long-range imaging down the pipe. In one embodiment, the method comprises: (a) extending an imaging head into the manhole using a positioning system, the imaging head comprising an imaging device and at least one lamp capable of producing a light beam, the positioning system comprising an elongated member and a targeting fixture operatively connected thereto, the imaging head being attached to one end of the elongated member, the targeting fixture having a distal end biased outwardly from the imaging head; (b) placing the distal end on a rigid surface proximate the lateral pipe; (c) pushing down on the elongated member such that the distal end resiliently moves toward the imaging head, thereby allowing the light beam to be centered approximately in the lateral pipe; and (d) imaging a target located within the lateral pipe.

Another aspect of the invention is a method of inspecting a pipe by adjusting the illumination source while imaging down the pipe to optimize the illumination of the target being imaged. In one embodiment, the method comprising: (a) inserting an imaging head into the manhole using a positioning system, the imaging head connected to an elongated member and comprising an imaging device adapted to convert an image to an image signal, a lens optically coupled to the imaging device, and at least one lamp suitable for projecting a light beam, the lamp having a beam that is adjustable to enable the beam to move relative the imaging device; (b) imaging a target located within the lateral pipe; and (c) holding the imaging device essentially steady while imaging the target and adjusting the beam to adjust the illumination of the target.

Yet another aspect of the invention is a method of inspecting a pipe in a manhole by adjusting the illumination source while imaging down the pipe to optimize the illumination of the target being imaged. In one embodiment, the method comprises: (a) extending an imaging system into a manhole; (b) imaging the interior of the manhole at a first magnification level of an imaging device; (c) locating a lateral pipe connected to the manhole; (d) imaging the interior of the lateral pipe at a second magnification level greater than the first level to image a target; and (e) adjusting a light beam being emitted from the imaging system to alter illumination of the target while holding the image of the target steady.

Another aspect of the invention is an inspection system for positioning the lights and imaging device in the sweet spot for enhanced long-range imaging down the pipe. In one embodiment, the system comprises: (a) an imaging head comprising an imaging device adapted to convert an image to an image signal, a lens optically coupled to the imaging device, and at least one lamp suitable for projecting a light beam; (b) a support system electronically connected to the imaging device for receiving the image signal from the imaging device and for transmitting a zoom signal to the lens to achieve the desired magnification; and (c) a positioning system comprising an elongated member and a targeting fixture, the upon which the imaging head is attached and adapted for handling to position the imaging head in a desired position to view the elongated structure, and a targeting fixture extending outwardly from the imaging head, the targeting fixture having a distal end being biased outwardly from the imaging head such that, when pushed against a rigid surface, the distal end moves resiliently inward thereby effectively adjusting the position of the lamp relative to the rigid surface.

Another aspect of the invention is an inspection system for enhanced long-range imaging down the pipe. In one embodiment, the system comprises: (a) a positioning system comprising an elongated member; (b) an imaging head connected to the elongated member and comprising an imaging device adapted to convert an image to an image signal, a lens optically coupled to the imaging device, and at least one lamp having an adjustable beam enabling the beam to move relative the imaging device; and (c) an operator control device separate form the imaging head to control the imaging device.

DETAILED DESCRIPTION

Figure 1:
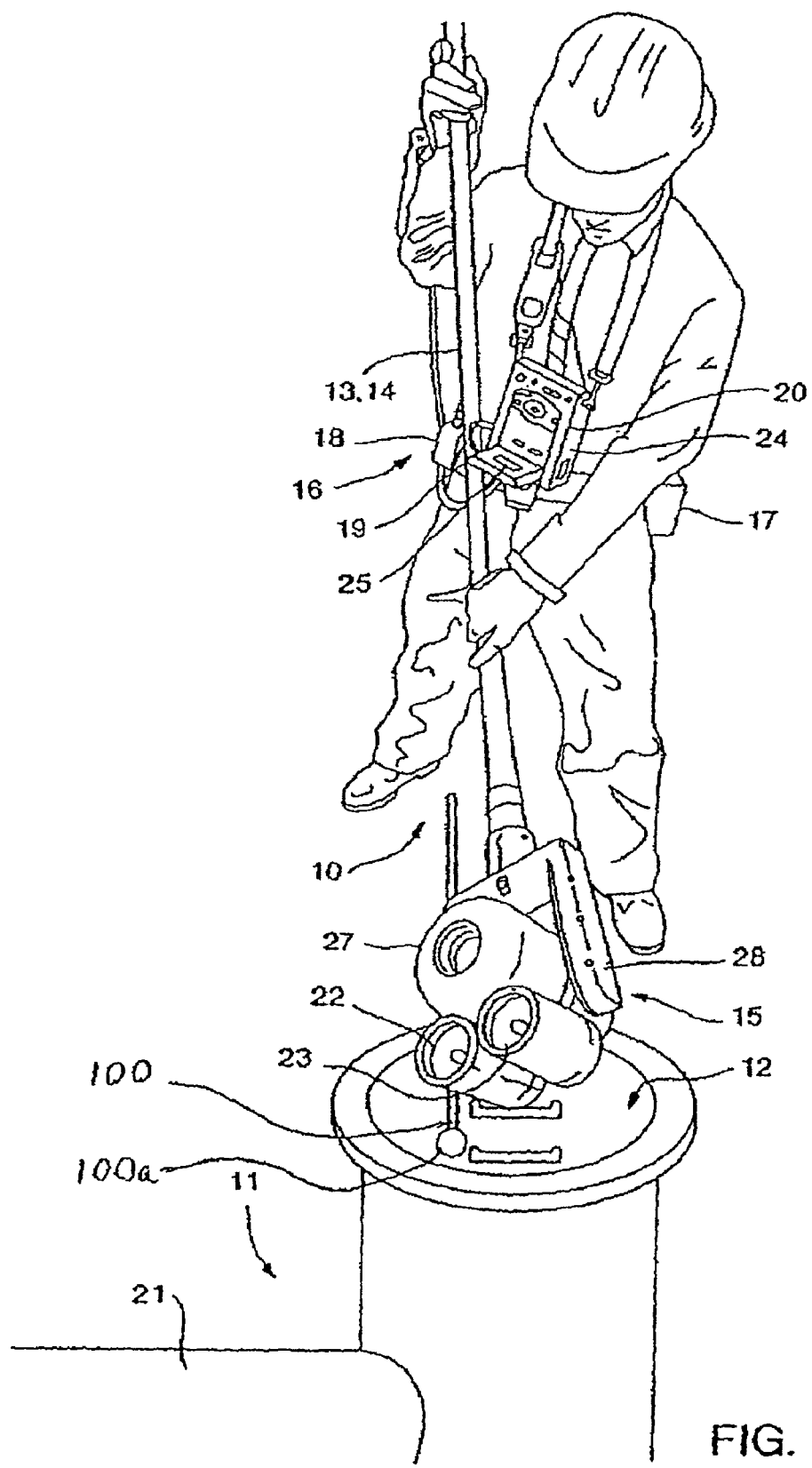
FIG. 1 shows a user inserting one embodiment of the device into a manhole.

Referring to the drawings, FIG. 1 shows a user operating one embodiment of the inspection system 10 to ascertain whether an invasive procedure is warranted. Using the system 10 comprises the steps of (a) extending an imaging head 15 into the manhole 12 using a positioning system 13, the imaging head 15 comprising an imaging device (within enclosure 27) and at least one lamp 23 capable of producing a light beam (not shown), the positioning system comprising an elongated member 14 and a targeting fixture 100 operatively connected thereto, the imaging head 15 being attached to one end of the elongated member 14, the targeting fixture 100 having a distal end 100a biased outwardly from the imaging head 15; (b) placing the distal end 100a on a rigid surface proximate to the lateral pipe 21; (c) pushing down on the elongated member 14 such that the distal end 100a resiliently moves toward the imaging head 15, thereby allowing the light beam to be centered approximately in the lateral pipe 21; (d) imaging a target located within the lateral pipe; and (e) optionally performing a more invasive procedure if necessary.

Each of these steps is considered in greater detail below. It should be understood, however, that the classification of the process in these discrete steps is for illustrative purposes and should not be construed to limit the scope of the invention. For example, it is anticipated that two or more steps may be performed in a single operation or one or more steps may not be performed at all.

With respect to step (a), the user lowers the imaging head 15 into a manhole 12 using a positioning system 13 while observing a monitor 25. The positioning system 13 in this embodiment comprises an elongated member 14, in one embodiment a telescoping boom, and the targeting fixture 100. Prior to inserting the imaging head 15 into the manhole 12, it may be preferable to calibrate the targeting fixture 100 for the diameter of the lateral pipe. This way, the imaging head is initially closer to the "sweet spot" (mentioned below in step (c)), requiring only slight deflection of the targeting fixture for fine tuning.

In step (b), the targeting fixture is placed on a rigid surface proximate the lateral pipe 21. The rigid surface may be, for example, the interior of the lateral pipe 21 at the junction of the manhole 12. To effect this placement, the interior of the manhole is typically imaged initially at a low magnification level, which provides a wide field of view. The user then inspects the manhole's condition and attempts to locate the penetration of the lateral pipe 21 in the manhole 12. It may be preferable to illuminate the interior of the manhole using a floodlight 22, which provides a wash of light commensurate with the wide field of view. Once the entrance to the lateral pipe 21 is located, the user positions the imaging head 15 with the interior of the lateral pipe 21 in its field of view.

In step (c), the user pushes down on the device 10 to resiliently deflect its distal end 100a such that imaging head 15 moves downward and into the "sweet spot." As mentioned above, applicant has discovered that enhanced imaging at longer ranges can be achieved by properly positioning the light beam within the pipe such that its incidence with the wall of the pipe is extended as far down the pipe as possible. If the pipe is essentially free of material, the sweet spot is in the center approximately of the pipe. If, however, the pipe is partially filled with material, particularly liquids which tend to reflect light, and then the sweet spot will be in the center approximately of the space above the material. (It should be understood that the term "center approximately" as used herein refers to a visual approximation of the center and should not be interpreted as a precise position. One of skill in the art will appreciate when the beam is centered approximately through visual estimation.)

In step (d), a target in the lateral pipe 21 is imaged. To this end, the user in one embodiment uses a joystick to zoom down the lateral pipe in auto focus initially. It is generally recognized, however, that auto-focus tends to be limited in range, and targets beyond a range of approximately 40 feet require manual focus. Accordingly, the user switches to manual focus, in one embodiment by depressing the joystick 600 (see FIG. 6). In one embodiment, the joystick also controls the manual focus. That is, in one embodiment, moving the joystick back and forth along one axis causes the zoom to go in and out, while moving the joystick from side to side causes the focus (i.e., the focal point) to move in and out.

While zooming, it is critical to illuminate the target to facilitate effective imaging. To this end, it may be preferable to illuminate the viewed area using a spot light 23 which provides a high intensity, relatively-focused light commensurate with the relatively narrow field of view associated with high-magnification. In one embodiment, spotlight 23 is a high intensity discharge lamp, which produces a particularly narrow beam. In a more preferred embodiment, the beam of spotlight 23 becomes narrower as the user zooms in at the target. This functionality is discussed in greater detail below.

While imaging the target in step (d) it may also be preferable to determine the range of the target. This can be done using known range finders such as a laser range finder. The ability of the inspection device of the present invention to focus on targets far down the pipe is particularly beneficial in this respect, as often such range finders require user to position a relatively small laser spot on the target to measure it.

In step (d), images of the interior of the lateral pipe may be recorded and stored on a computer readable medium. In this embodiment, a digital image is captured with a frame grabber 24 and stored on a disk (not shown). It may be preferable to store the digital information in a database along with data corresponding to the location of the imaged area. This location data may be, for example, a manhole number or designation, a street address, global coordinates, or map coordinates. In one preferred embodiment, the inspection system generates global coordinates using an onboard global position system (GPS). These coordinates are then stored along with the image in a database such that, when a particular imaged is viewed, its corresponding location is also displayed. It may be preferable to display the imaged area's location in the form of a reference point on a map. Displaying an object's position on a map using GPS coordinates is well known and systems for doing so are commercially available though such companies as Garmin and ESRI. In one particularly preferred embodiment, the image of the area is displayed on the region of a map corresponding to the area's location.

Once the images are obtained, they may be analyzed on-site or off-site to determine whether an invasive procedure is required. In the latter situation, it may be preferable to transmit a digital signal of the image over a telecommunication link (e.g., the internet) to the off-site location. Accordingly, one embodiment of the present invention enables a user to obtain quickly and conveniently digital images of lateral pipes for evaluation before invasive procedures are used.

In step (e), an invasive procedure may be undertaken to resolve the problem or further assess it. For example, if a crack is detected, a more comprehensive inspection may be performed in which an invasive inspection device, such as a pipe crawler or push camera, is introduced in the pipe to obtain detailed images pursuant to formulating a plan to remedy the situation. Likewise, if the initial inspection detects that a pipe is clogged, it may be cleaned contemporaneously by introducing an invasive cleaning device into the pipe to remove the obstruction. Given the convenience of the inspection system of the present invention, it is preferred that pipe cleaning procedures be modified to include follow-up inspections immediately after cleaning rather than calling in a specialized inspection team. In this respect, it may be preferable to physically integrate the inspection system with the cleaning system.

Aside from enhanced imaging range, Applicants have discovered a number of unexpected benefits and synergies of operating in the sweet spot. For example, operating in the sweet spot promotes the use of a lamp having narrow spot beams since they can be effectively aimed for maximum propagation. Previously, narrow spot beams were ineffective since they would reflect off the wall of the pipe and diffuse before their long range benefits could be realized. Therefore, operating in the sweet spot enables a high intensity beam to reach a long-range target to facilitate imaging. Once the target is properly illuminated, the image can be focused. To this end, the present invention also provides for a convenient focusing device that allows the target to be magnified and manually focused with ease. Obtaining a clear image of the target in turn allows data such as target dimensions and range to be determined. More specifically, any long range distance or size measurement depends on a well lit and steady image—accuracy of the survey depends upon it. Today the range of the range finder is far greater than the range of the camera and lighting. Accordingly, the combination of a range with a system having enhanced illumination and imaging is particularly synergistic.

Although FIG. 1 depicts the inspection of a pipe 21 through a manhole 12, it should be understood that the present invention is applicable to the inspection of any area located in an inaccessible and/or uninhabitable location as described above. For example, the device may be used to quickly and conveniently inspect the containment of a nuclear reactor without erecting scaffolding. By performing inspections quickly without extensive set-ups, the overall radiation dose incurred by personnel is reduced. Additionally, in addition to nuclear reactors, the inspection system of the present invention can be used in a host of other applications including, for example, the inspection of snubbers, pipe hangers, pipe insulation, storage vessels, and the like which are commonly found in power generating stations (such as fossil fuel, nuclear, and hydro), refineries, and, practically speaking, any other significant industrial facility. Furthermore, aside from industrial applications, the system of the present invention may be used for examining vehicles or structures for evidence of terrorist activity. For example, rather than crawling under a truck or entering a confined space that might contain a bomb or biological threat, the inspection system may be used first to determine whether a closer inspection or perhaps robotic intervention (e.g., bomb defusing) is required.

Figure 7:
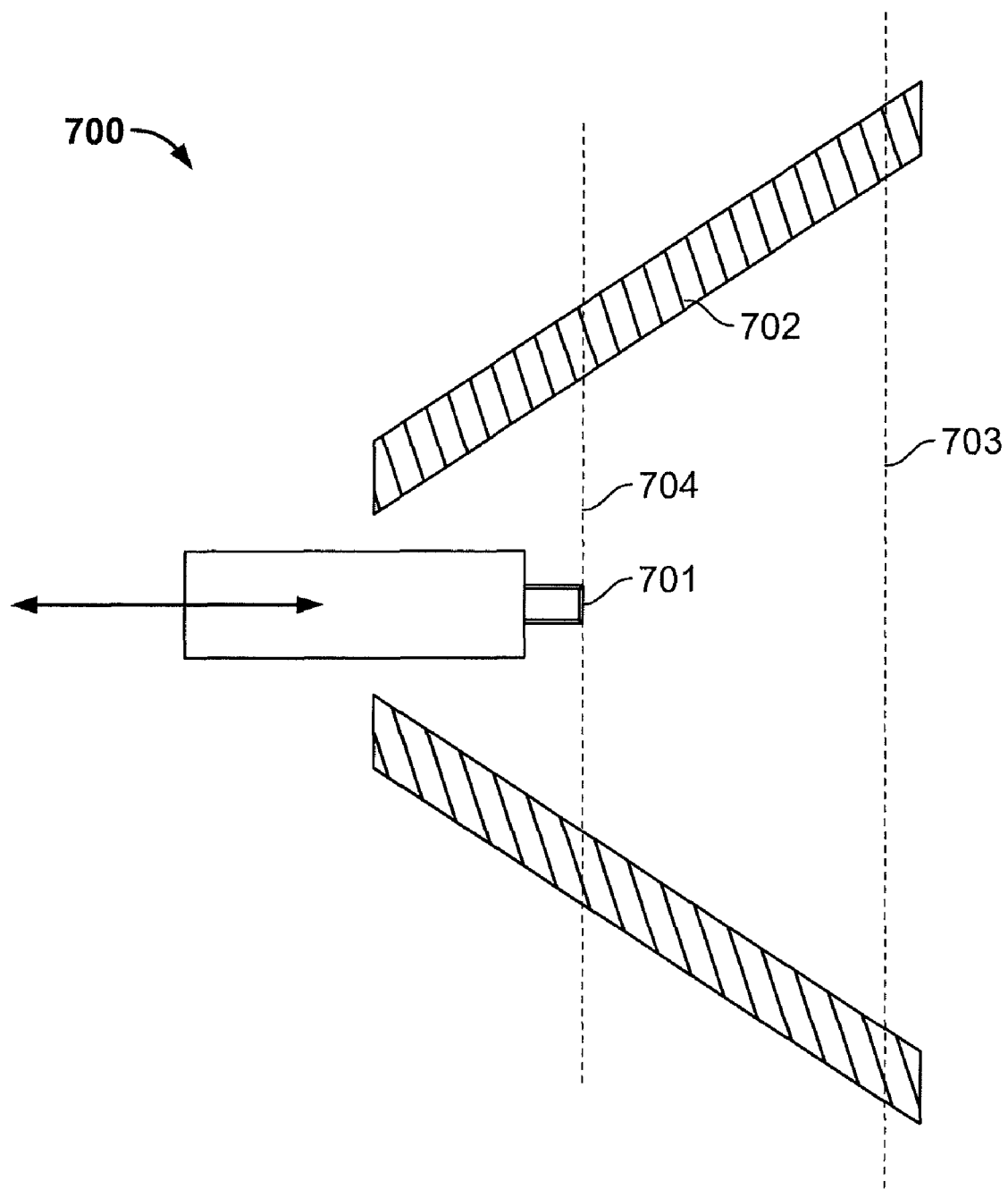
FIG. 7 shows a schematic of an adjustable beam lamp.
Figure 8A:
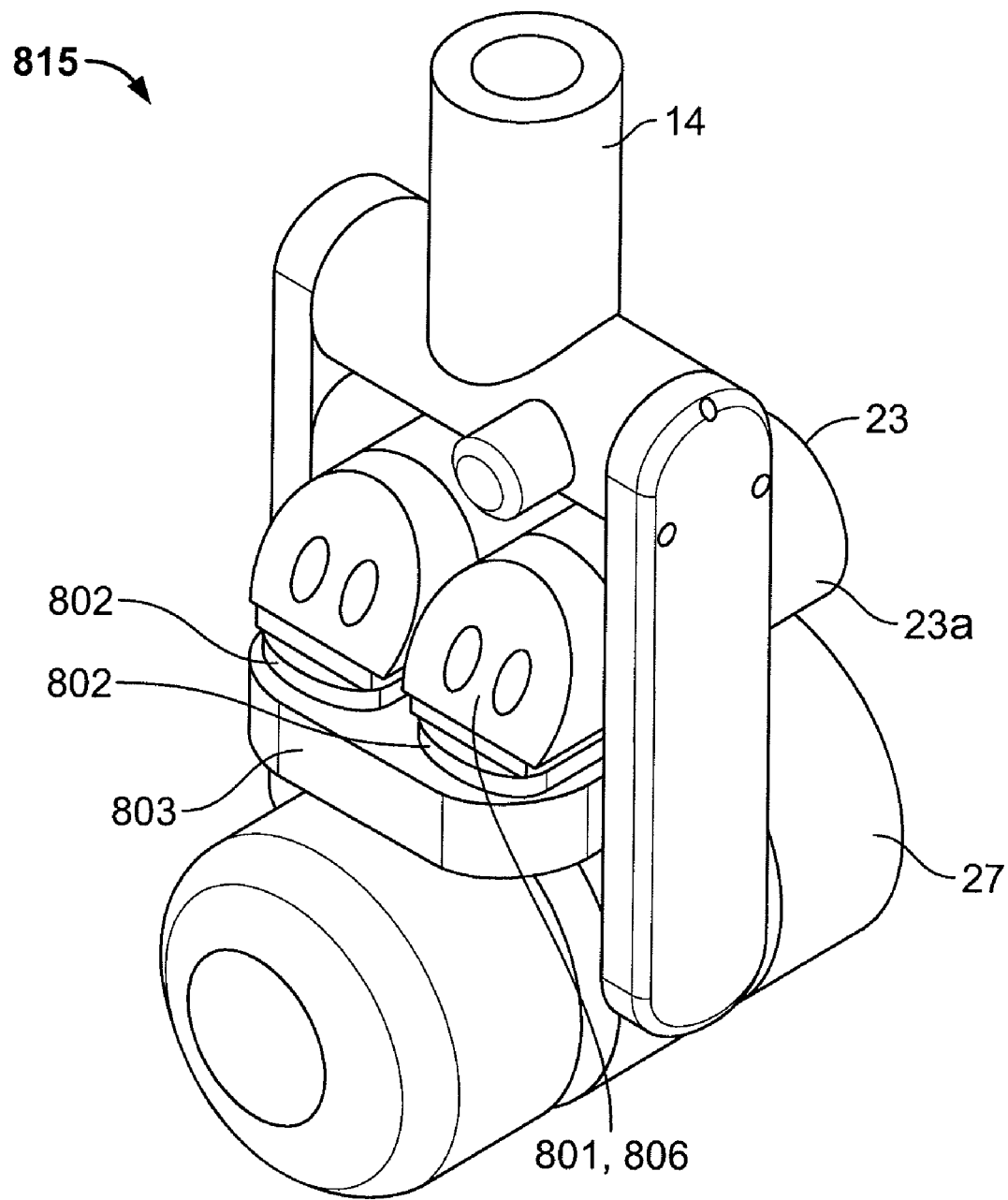
FIGS. 8a & 8b show different perspective views of an imaging head with a lamp adjustment mechanism.

Referring to FIGS. 1, 7 and 8(a) & (b), another embodiment of the invention is shown. This embodiment is similar to that shown in FIG. 1, but includes a lamp having an adjustable beam to enable beam to move independently of the imaging device. In one embodiment, the method comprising: (a) inserting an imaging head 15 (FIG. 1), 815 (FIG. 8(a)) into the manhole using an elongated member 14, the imaging head 15, 815 being connected to the elongated member and comprising an imaging device (not shown) adapted to convert an image to an image signal, a lens optically coupled to the imaging device, and at least one lamp 23 (FIGS. 1 and 8(a)), 700 (FIG. 7) suitable for projecting a light beam, the lamp having a beam that is adjustable enabling the beam to move relative the imaging device; (b) imaging a target located within the lateral pipe; and (c) holding the imaging device essentially steady while imaging the target and adjusting the beam to adjust the degree of illumination of the target.

This method is similar to that described above but involves adjusting the light beam to enhance the illumination of the target. Preferably, the light beam is adjusted to maximize the illumination of the target.

The light beam may be adjusted in different ways. For example, it may be preferable to automatically adjust the beam to maximize the luminance of the image. To this end, an IRE or similar component may be used to measure the amplitude of the luminance of the composite signal while the beam is being moved. The beam is then moved to the position in which the luminance peaks. Such techniques for measuring luminance in images are well known and can be performed in a microprocessor located at the imaging head 815, at the operator control, or in a peripheral device. If the adjustment of the lamp beam is automatic, it may be desirable to manually initiate the auto-adjustment once the target is imaged to avoid the lamps/beams moving while the imaging head is being positioned to image the target.

In another embodiment, the lamp beam is automatic, but is responsive to a signal from zoom signal, rather than, or in addition to, a luminance value. Specifically, the beam is adjusted to converge on the optical axis as the magnification is increased. This may be performed, for example, by angling the beam as disclosed in the embodiment of FIGS. 8(a) & (b), or narrowing the beam as disclosed in the embodiment of FIG. 7.

In yet another embodiment, the lamp beam is adjusted by the user manually using an operator control device. Specifically, the user may use a joy stick or similar device to move the beam while viewing the target.

The pattern in which the light beam moves either automatically or manually may be configurable. For example, it may be preferable to move the beam so that it cycles through converging and diverging with the optical axis. This may be accomplished by having the beam move inwardly and downwardly and then outwardly and upwardly in diagonal movement. Still other patterns of movement such as ellipses or circles may also be used. Alternatively, as shown in FIG. 7, rather than having the beam move up/down, side-to-side, or diagonal, it may be preferably to have it broadened and narrowed by moving 701 forward and backward respectively.

Figure 9:
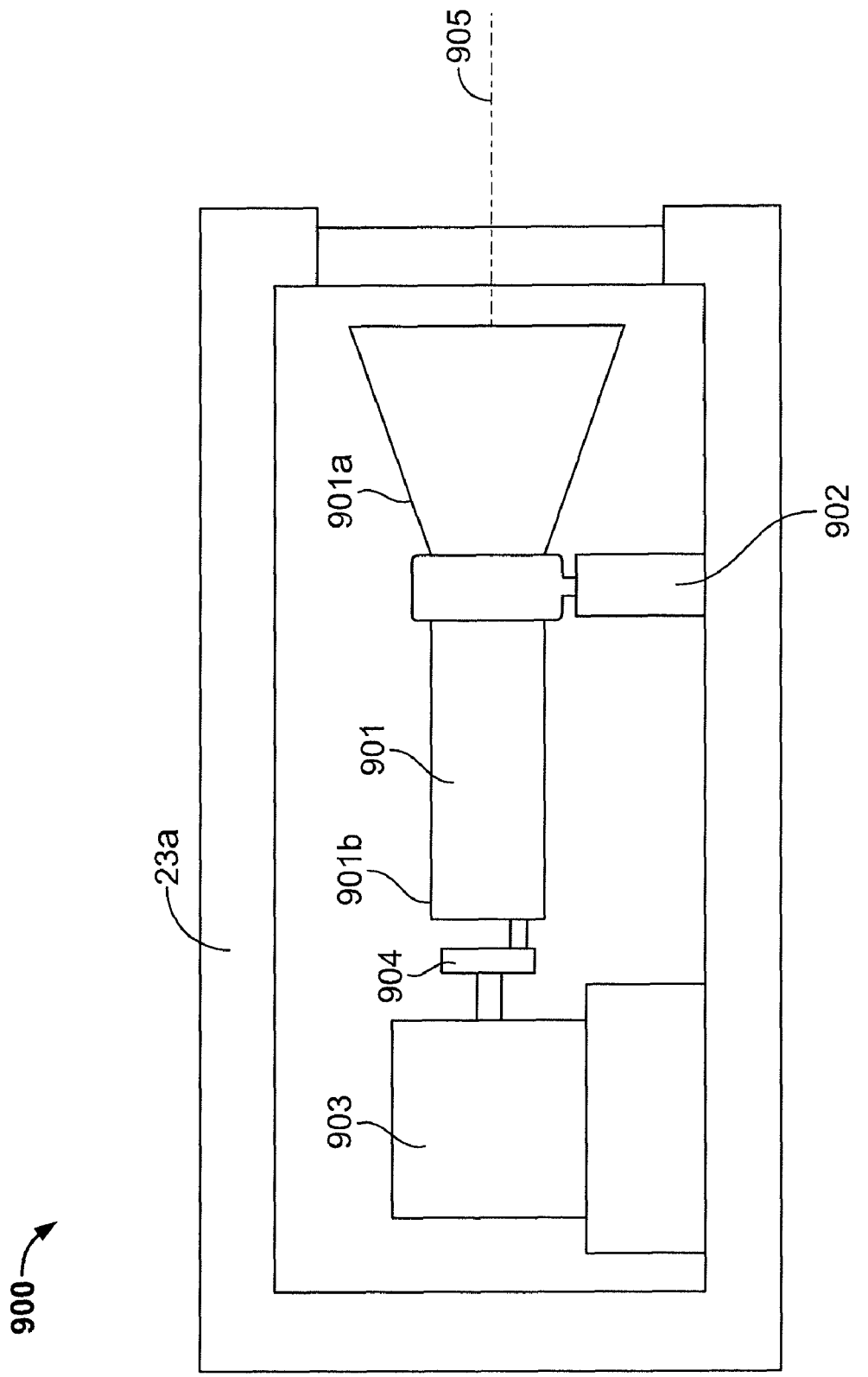
FIG. 9 shows another embodiment of an adjustable beam lamp in which the lamp moves within its housing.

The beam may be moved by either moving the lamp or moving components within the lamp. For example, referring to FIG. 8(a), the lamps 23 are mounted on a lamp adjustment mechanism 801, which in turn is mounted on the enclosure 27. As the lamp adjustment mechanism 801 pivots/rotates, the lamps 23 mounted to it move as well causing the beams to move independently of the imaging device contained within the enclosure 27. In another embodiment, the lamp is moved within the lamp housing 23a as discussed with respect to FIG. 9 below. Alternatively, the beam can be adjusted by moving components in the lamp 23. For example, referring to FIG. 7, the beam is broadened and narrowed by moving 701 forward and backward respectively.

In one embodiment, a plurality of lamps are connected to the imaging head. If the lamps are adjustable by virtue of their movement (rather than internal components as shown in FIG. 7), then the lamps are preferably spot lights. The lamps may be configured to move together or independently. If they move together, the lamps may move in the same direction or in different directions. For example, they may move in different directions to converge on the optical axis if they lamps are positioned on different sides of the optical axis as shown in FIG. 8(a).

Figure 2:
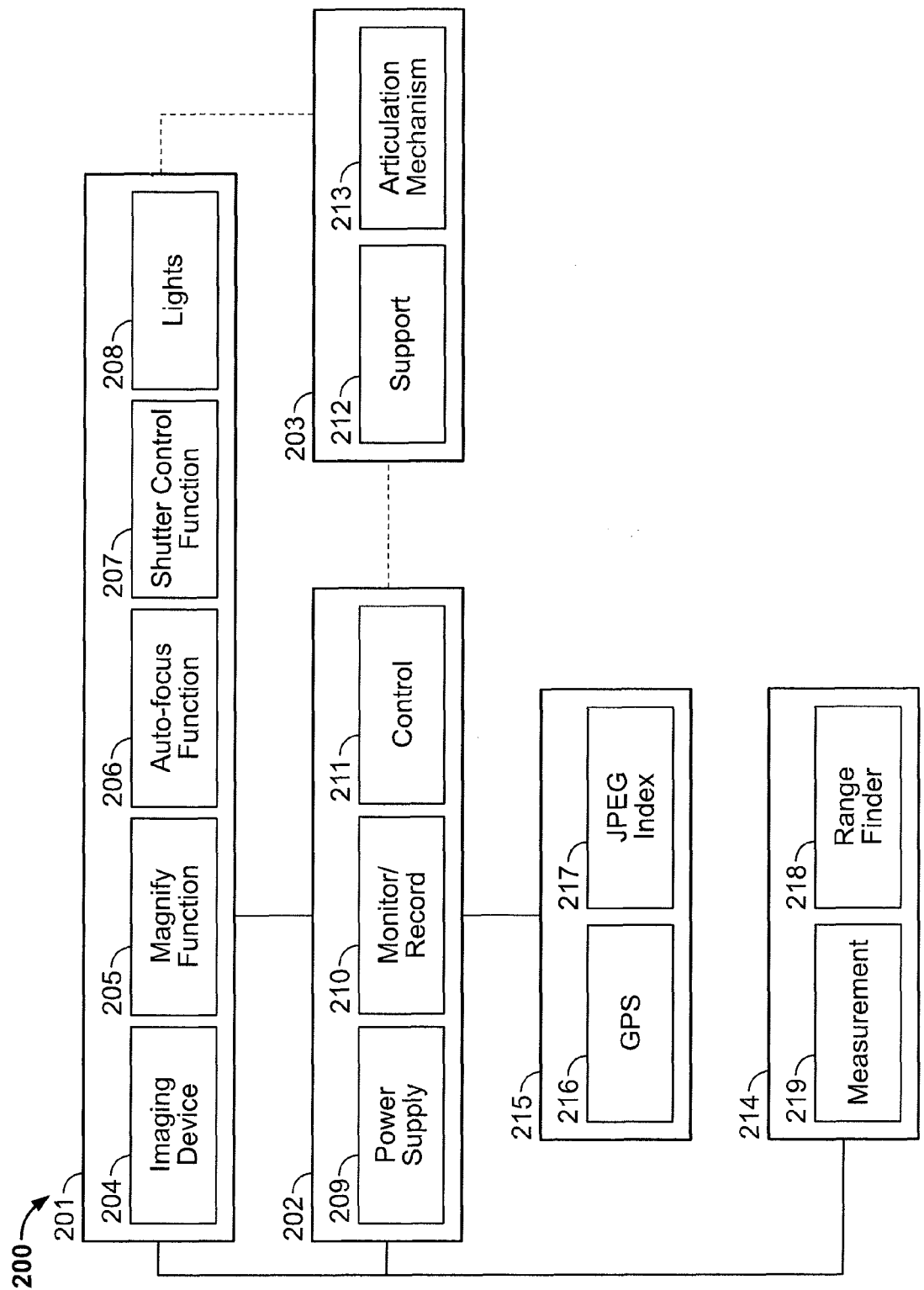
FIG. 2 shows a schematic of the system.

Now referring to FIG. 2, the subsystems of the inspection system will be described in greater detail. For illustrative purposes, the system 200 may be divided into the following subsystems: (1) the imaging head 201, (2) the support system 202 for supporting the functionality of the imaging head 201, (3) the positioning system 203 for physically positioning the imaging head 201, and, optionally, (4) a location system 215 for providing location data on the imaging head 201 and (5) a measuring system 214 for providing range and/or dimensional information of the images generated by the imaging head 201. It should be understood that the division of the system into various components is for illustrative purposes and should not be construed to limit the scope of the invention. Indeed, the various systems may be further divided into additional subsystems, or their various components and functions may be combined and integrated.

1. Imaging Head 201

The function of the imaging head is to generate and transmit an electrical signal corresponding to an area being imaged, herein referred to as the "image signal." The heart of the imaging head is an imaging device 204, which translates an image to an electrical signal. The imaging device 204 may be any conventional or subsequently-developed device for imaging a target object. The term "imaging" broadly refers to a characterization or representation of the target object based on a particular property, such as, for example, its tendency to reflect or absorb electromagnetic radiation, its thermal profile, or its acoustical profile. Devices for imaging these characteristics or properties are known and include, for example, video cameras, still cameras, digital cameras, infrared detectors, X-ray machines, lasers, microphones, sonic or ultrasonic transducers, radar, and the like.

In one embodiment, the imaging device 204 provides a video image of the target area. More preferable, the imaging device comprises a charge coupled device (CCD), which is well known in the art. The CCD electronically captures an image of the video field in an analog format and the analog information is relayed to the monitor/digital recording functionality 210 of the support system 202. In one embodiment, the CCD is a low-lux CCD having a sensitivity of at least 2 Lux at f1.4, and, more in one embodiment, at least 1 Lux at f1.4.

The imaging head 202 also includes magnification functionality 205 comprising one or more lenses having inherent optical characteristics such as distortion, focal length, and field of view, some of which are used in the calculation of the target size as is described in detail below. The preferred optical characteristics of the imaging head include a focal length of about 4 mm to about 74 mm, a field of view of about 2.7° to about 48°, and a minimum focal distance of about 10 mm to about 800 mm. The magnification functionality comprises a series of lenses that interact to change the focus and magnification. As is known in the art, the system includes motors that manipulate the positioning of the various individual lenses in relation to each other and in relation to the CCD in order to effect different foci and magnification configurations. These motors are responsive to a zoom signal from the support system.

The magnification functionality 205 is capable of achieving a relatively high magnification ratio. More specifically, the intended applications of the inspection system of the present invention usually require a panoramic, wide angle view for general viewing, and a magnified view for details. Again, such functionality is well known in the art and may comprise, for example, optical magnification or electronic magnification using techniques such as pixel enlargement or interpolation. In one embodiment, the magnification has a magnification ratio of no less than about 6:1, more In one embodiment, no less than about 12:1, and even more preferable, no less than about 50:1. In a highly preferred embodiment, the magnification ratio is 216:1 and is the composite of an 18:1 optical zoom and a 12:1 digital zoom. It is anticipated that even high magnification ratios may be used. For example, magnification functionality having a ratio of 432:1 (composite of 32:1 optical and 12:1 digital) is currently available.

The imaging head, in one embodiment, comprises auto focus functionality 206. Again, auto focusing is known in the art. More In one embodiment, the imaging head provides for manual focusing thereby allowing the user to control the focus if, for example, the auto focus is focusing on the wrong object or the range of the target is too far under high zoom conditions. In one embodiment, the focus and zoom motors contain servo-feedback mechanisms, which provide information to a microprocessor.

In one embodiment, the imaging head also enables the user to control the shutter speed manually through shutter control functionality 207. More specifically, in certain applications, for example, in low light conditions, it may be desirable for the user to extend the exposure time to increase the amount of light in the image. For example, shutter speed may be increased from a typical period of about 1/50 second to about 1/3 second.

Suitable imaging heads having the above-mentioned magnification and functionality are commercially available from, for example, Sony Company (Model No. FCB-IX47).

Figure 6:
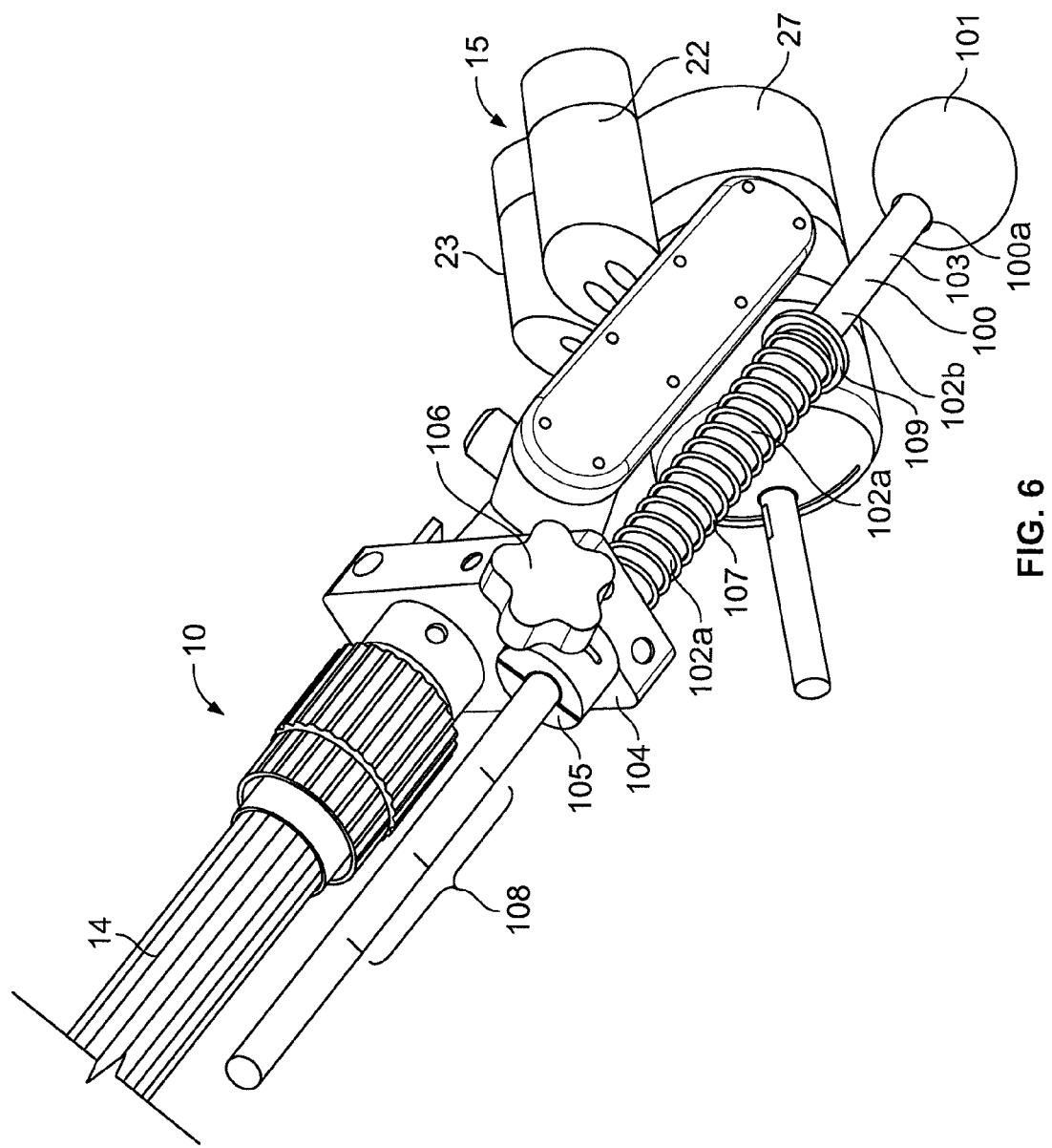
FIG. 6 shows a close up perspective view of the imaging head with targeting fixture.

In one embodiment, the imaging device and the above-mentioned functionality are integrally packaged in a module, which, in turn, is contained within a head enclosure 27 or simply "head" (see FIG. 6). In one embodiment, the enclosure 27 is splash proof, and, more in one embodiment, the enclosure is sealed and watertight thereby allowing it to be submerged. To this end, it may be desirable to pressurize the enclosure to match the anticipated hydrostatic pressure to minimize the risk of leakage.

In one embodiment, the module is mounted to the enclosure such that variation between the relative position of the module and enclosure is minimized. That is, applicant recognizes that it is critical that the imaging device be precisely positioned within the head enclosure 27 since a small degree of variation can have a profound impact at high magnification. For example, a one degree variation in camera position equates to 30 inches at 150 feet. To avoid this variation, applicant has found that it is preferable to attach the lens of the module to the enclosure rather than the shielding that encloses the imaging device since the shielding is typically formed of flimsy material, which deforms easily during installation. If the lens is aligned precisely relative to the head enclosure, than the imaging device is aligned because the image device is optically coupled to the lens with high precision.

Figure 8B:
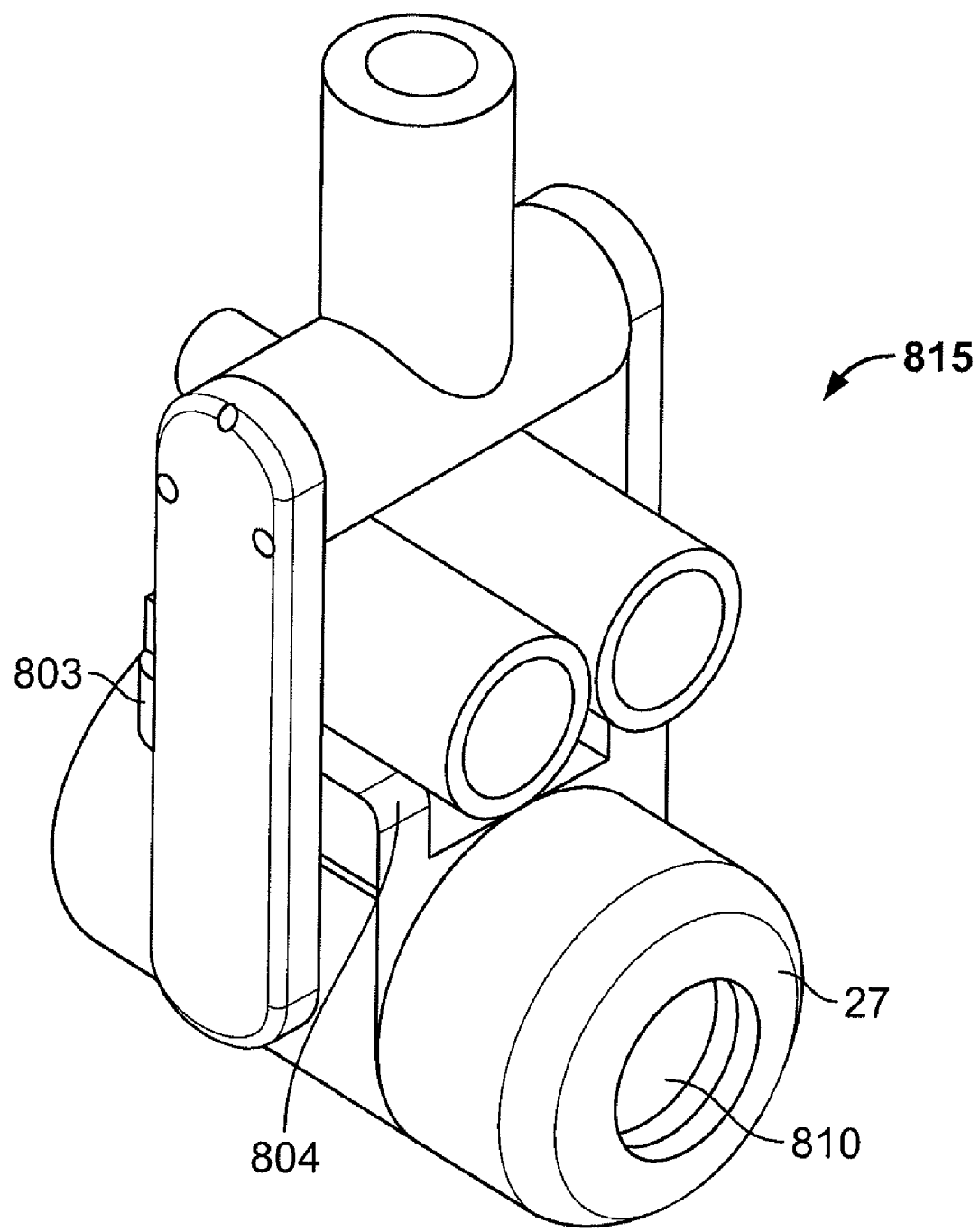

In one embodiment, both the lamp and the imaging device are registered to the enclosure of the imaging head. If the lamp and the imaging device are both aligned with respect to the enclosure of the imaging device, then the two components will also be alignment. One way to achieve this alignment is to secure the imaging device securely in the enclosure such that the position of its lens is essentially "locked" in place in the enclosure. More specifically, an enclosure is provided having a contoured perimeter 810 (see FIG. 8b). The perimeter is contoured to cooperate with the contour of a lens assembly holding the lens of the imaging head such that essentially no relative movement of the lens and enclosure 27 is allowed once the perimeter 810 receives the lens assembly. This cooperating contours may be, for example, an annular groove in the perimeter to receive an annular ring of the lens assembly (or visa versa), a rabbited seat in the perimeter to receive an edge of the lens assembly (or visa versa), cooperating spline or key assemblies, or any other mechanisms know for aligning one component to another. Additionally, the enclosure may be manufactured such that it holds the lens assembly and imaging device snuggly, thereby allowing essentially no movement of the imaging device relative to the enclosure. This avoids the need for flimsy sheet metal supports to connect the imaging device to the enclosure. Thus, this assembly provides an imaging device and lens train that is registered in tight tolerance with the enclosure. This way, if the lamps are also secured to the enclosure with tight tolerance, the lamps and imaging device will be closely aligned.

In one embodiment, the imaging head comprises one or more lights 208 (22, 23 in FIG. 6) to illuminate the target area and improve the quality of the images obtained. Given the relatively high magnification ratios of the imaging head, in one embodiment, the imaging head comprises at least two types of lights, a flood light 22 and a spot light 23. The function of these lights is well known in the art. Specifically, a flood light is useful for illuminating a relatively close, broad area, while a spot light illuminates a focused area at a further distance. The lights may be packaged individually or in combination, and may be integral with the head enclosure 27 or separate therefrom.

In one embodiment, the spot light is a high intensity discharge lamp rather than a halogen lamp. Suitable lamps are available. It has been found that such lamps are particularly suited for inspection applications since they have higher color temperature, a narrow beam, and greater lumen output per watt. Specifically, since they have improved color temperature, they enhance imaging even at lower light levels, which are common in pipe imaging. It has been found also that the narrow arc of high intensity discharge lamps (approximately 2 mm) results in a narrow beam, even with a traditional 6 degree reflector. Narrow light beams are necessary for long-range imaging in pipes. Further, the low power consumption translates into lighter (thinner) power cable and longer battery life. In fact, given their relatively low energy consumption, a number of lamps having different beam sizes can be used to illuminate different ranges of the pipe in place of a signal halogen. For example, one lamp can be tuned for 0-50', another for 50-100', and a third for 100-150'.

As mentioned above, in one embodiment, the lamp 23 has an adjustable beam, enabling the beam to be moved independently of the imaging device. For example, in one embodiment, the variable spot light comprises a high intensity discharge element to generate the light. For example, referring to FIG. 7, a schematic of a variable beam lamp 700 is shown. The element 701 is axially moveable within a conically (i.e., conical, elliptical, hyperbolic, parabolic) shaped reflective element 702. As the element moves from the broader portion 703 of the reflective element 702 to the narrower portion 704, the beam narrows in kind. In one embodiment, the element is actuated axially in accordance with the zoom so that, as the user zooms in, the element retracts into the conical reflector to narrow the beam. This way the beam is matched to the zoom. In one embodiment, the same zoom signal is used to control both the variable beam lamp and the magnification functionality. This consolidation of lighting has a number of important benefits including reducing the size and weight of the imaging device 15 and reducing energy requirements.

In another embodiment, the beam is adjusted by moving the lamp(s) independently from the imaging system. To this end, the imaging head comprises a lamp adjustment mechanism 801 interposed between the lamp and the enclosure to allow the lamp(s) to move relative to the imaging device. The lamp adjustment mechanism 801 may be any know device for allowing relative movement along at least one axis. Suitable mechanisms include, for example, pivots, ball and socket assemblies, hinges, swivels, trunnions, gimbals, turrets, cams, and combinations of such mechanisms. In one embodiment, the mechanism 801 is a pan-and-tilt mechanism 806, which comprises turrets 802 for allowing the lamps to rotate on a vertical axis and a tilt pivot 804 for allowing a platform 803 on which the turrets are mounted to pivot up and down. Such pan-and-tilt mechanisms are well known and available in various configurations.

Rather than having the housing 23a of the lamp 23 move to effect the beams movement, it may be beneficial to have the lamp 23 move within the lamp housing 23a. For example, referring to FIG. 9, a schematic of one embodiment of an adjustable lamp assembly 900 is shown. As shown, the lamp 901 in contained within the lamp housing 23a, with its front end 901a being supported by a swivel 902. A motor 903 is disposed in back of the lamp 901 but within the housing 23a. The motor has a shaft 904 that is offset from optical axis 905 of the lamp. The shaft is connected to the rear end 901b of the lamp 901 by a connector 906. As the motor turns the offset will cause the lamp to oscillate. Given that the amount of required movement of the lamp is very small, some kind of gear reduction or similar mechanism may be desirable such that the lamp moves slowly in response to the motor rotating. Still other embodiments for moving the lamp 901 within the lamp housing 23a will be know to those of skill in the art in light of this disclosure. For example, rather than using an offset between the motor shaft and the optical axis 905 a cam mechanism may be used.

In one embodiment, the lamp adjustment mechanism is controlled by a manual control on the operator's control device. In another embodiment, the lamp adjustment mechanism is controlled automatically by one or more processors configured to determine the luminance of an image generated by the imaging device and to send a signal to actuate the lamp adjustment mechanism until luminance is maximized. In such an embodiment, it may be preferable to configure the processor(s) to initiate the auto-adjust feature only after receiving a signal form the operator to avoid a situation in which the lamps are adjusting while the imaging head is still being positioned.

In one embodiment, the system comprises two spot lamps. In one embodiment, each lamp has a lamp adjustment mechanism to enable each lamp to move independently of each other. In another embodiment, the lamps share a common lamp adjustment mechanism so that they move together. In one such an embodiment, the lamp adjustment mechanism has one or more gears configured such that movement of the lamp adjustment mechanism results in different movement of the lamps.

2. Support System 202

The support system 202 is a portable system and functions to support the functionality of the imaging head 201. Supporting the functionality of the imaging head requires providing the imaging head with power and control signals. To this end, a preferred support system comprises a power supply 209, operator's control 211, and monitoring/recording functionality 210.

Figure 4:
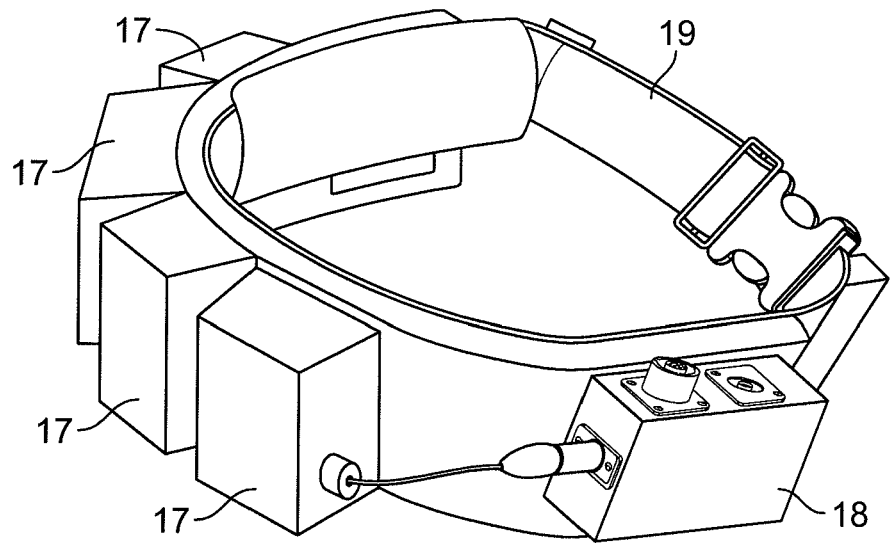
FIG. 4 shows the belt of one embodiment of FIG. 1.

In one embodiment, the power supply and operator's control are mounted on a belt 19, as shown in FIG. 4, which is adapted to be worn by the user. Alternatively, a vest may be used. The power supply 209 supplies power to the imaging head and to other components of the support system requiring power. In one embodiment, the power is supplied by one or more rechargeable batteries releasably mounted to the belt 19 as shown in FIG. 4. Given the weight of batteries, particularly wet cells, it may be preferable under some circumstances to place one or more batteries on the ground during operation of the inspection system. Although rechargeable belt-mounted batteries are preferred, power may be provided through other conventional means such as a portable generator.

Figure 3A:
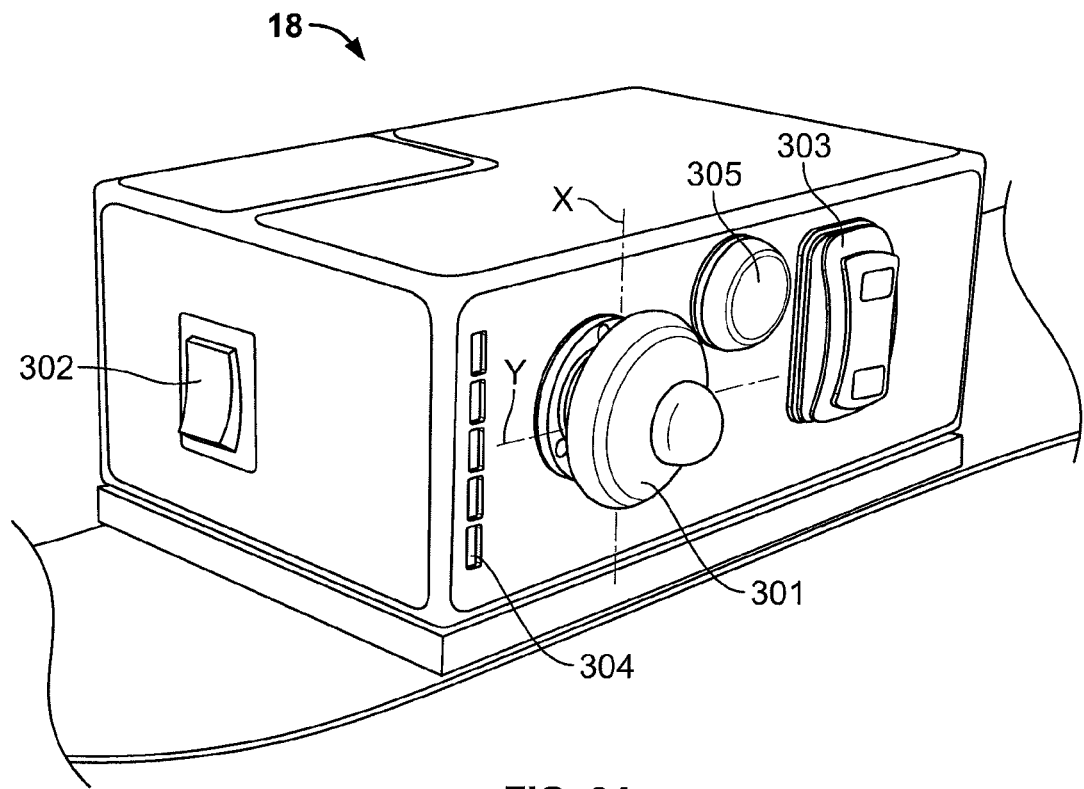
FIGS. 3(a) & (b) show different perspective views of the operator's control in one embodiment of FIG. 1.

The operator's control 18 is used to control the on/off operation of the imaging device as well as the other functions such as magnification, manual focus and shutter speed, and lights. In one embodiment, this control functionality is integrated into a single enclosure as shown in FIGS. 3(a) and (b). This enclosure is adapted to be mounted to the belt 19 as shown in FIG. 4.

As shown, the operator's control 18 comprises controls for power, zoom, focus, and lighting, and a monitor for battery life monitor. Specifically, the power to the imaging head is controlled by switch 302, and a series of LEDs 304 are used to provide an indication of battery life.

In one embodiment, a single joystick 301 is provided to control both the magnification and manual focus. Specifically, the joystick is actuateable along perpendicular x and y axes, such that movement along the one axis controls the zoom while movement along the other controls the focus. As view in FIG. 3, movement along the x axis in one embodiment controls focus, while movement along the y axis in one embodiment controls zoom. In one embodiment, the joystick 301 is actuateable perpendicular to the x and y axes to swith the imaging head between auto and manual focus. This allows the user to simply push down on the joystick to switch between the functions.

In another embodiment, the joystick not only controls the zoom, but also the beam size of the spot light 23. As the joystick is moved to transmit a zoom signal to zoom in on a target, the same or related signal is transmitted to the variable spot light causing its beam to narrow. By having the zoom and the beam sized linked, applicant finds that a single light can provide for all the lighting needs of the system. This simplifies not only the hardware requirements of the imaging head as described above, but also the operation of the device as there is no need to switch between different lamps or attempt to correlate the right lighting with the desired zoom.

In an embodiment having dual lights (i.e., flood and spot), the operator's control 18 In one embodiment comprises a three-position rocker switch 303 with LED indicator lights for light control such that when one side is depressed the flood light is on, when the other side is depressed the spot light is on, and when in the middle, both lights are off.

In one embodiment, the operator's control also comprises a switch 305 for controlling the light sensitivity of the imaging device. This is a known feature (see above shutter control functionality 207 mentioned above), which allows the imaging device to image a target in the event of diminished lighting conditions or shadows.

Figure 3B:
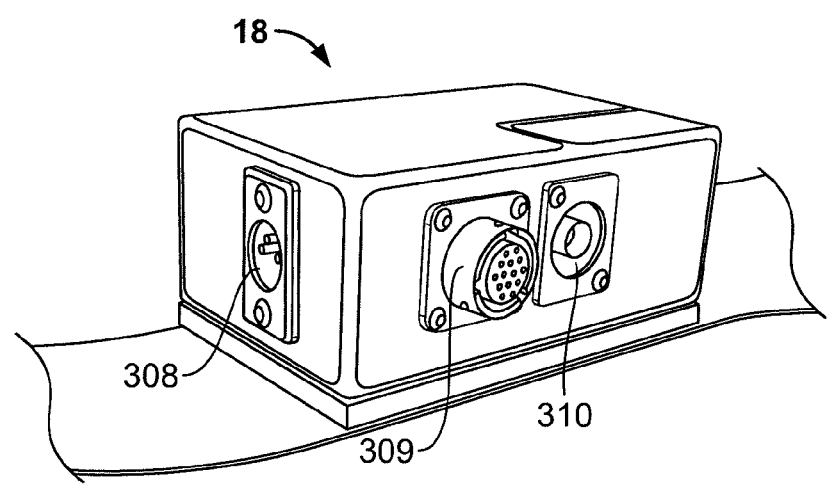

FIG. 3b is the other side view of the operator's control and shows the power input 308 to supply power to the various control functionality, and an input 309 for the video signal from the imaging head, a video output 310 to the monitor/recorder/frame grabber (described below).

The operator's control comprises a circuit board that interfaces the various control functionality and transmits commands to and receives acknowledgments from the imaging head. In one embodiment, the circuit board comprises a programmable controller (IC1A). The programmable controller provides for configurable control functionality where the function of the switches described above may be reconfigured through a simple software or firmware change. Although the control functionality may be hardwired directly to the imaging head, interfacing the imaging head through a circuit board having a programmable controller is preferred from a flexibility standpoint. Additionally, the communication link between the control functionality and the imaging head may be metallic or wireless, although metallic is preferred.

Figure 5:
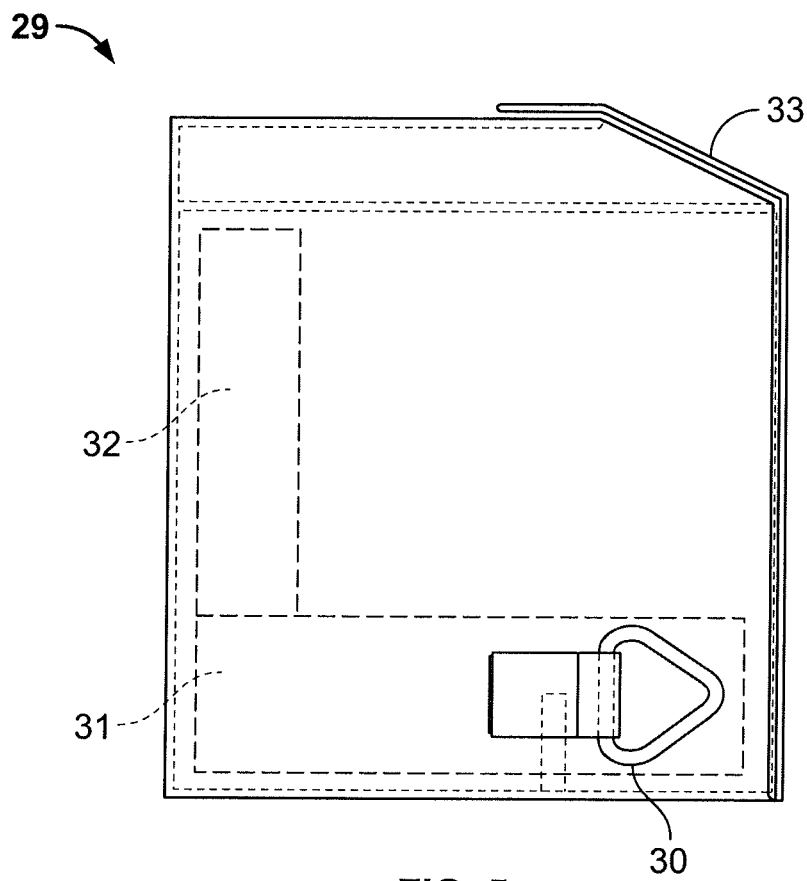
FIG. 5 shows a bag for supporting a monitor/recording device.

Referring back to FIG. 2, the output device 210 In one embodiment comprises a monitor, which allows the user to view the images being transmitted by the imaging head in real time. Such a function is highly preferred as it provides feedback to the user as he or she positions the imaging head. Monitoring devices are well known in the art. In one embodiment, the imaging head is lightweight and supported in such a way as to allow the user to view it conveniently while operating the positioning system. More In one embodiment, the monitor is worn around the user's neck as shown in FIG. 1. Still more in one embodiment, the monitor is contained in a bag or similar device to provide shielding from the sun to improve visibility and reduce glare. For example, the monitor/recording functionality may be supported by a bag 29 as shown in FIG. 5 adapted to be worn around the user's shoulders/neck. The bag 29 In one embodiment has a hook & loop fastened flap 33 and is configured to support a recording device 31 and a monitor 32 (shown in dotted lines).

In one embodiment, the output device 210 comprises a recording device for recording one or more images for evaluation later. In one embodiment, the recording device is a digital frame grabber. The frame grabber is adapted to convert an analog signal to a digital image and conveniently store the image on a computer-readable medium such as a disk. The Images may be still images or video images. Images may be stored, for example, in JPEG or a bitmap format, which is readily-transmitted over conventional telecommunication links anywhere in the world without loss of resolution. It has been found that having images in such a readily-transmittable form provides others, who need not be on-site, with the opportunity to analyze the images and determine whether an invasive procedure is required while personnel are on site and in position to perform such a procedure.

In one embodiment, the monitor and frame grabber are integrated into a single unit to provide for a conveniently transportable package. Suitable monitors/frame grabbers are commercially available from, for example, Sony Company (Model No. MVC-FDR3).

Alternatively or additionally, another type of recording device may be used. For example, it may be preferable under certain circumstances to use a video tape recorder. Suitable monitor/tape recorders are commercially available from, for example, Sony Company (Model No. GV-D900).

3. Positioning System 203

The positioning system 203 functions to position the imaging head 15 to image the desired area or target. Since the inspection system of the present invention is intended to inspect hard-to-reach areas or areas, which are generally inaccessible to humans, it is preferable for the inspection system to be highly maneuverable. In one embodiment, the positioning system comprises a support 212, more in one embodiment an elongated member, which has the head of the imaging head mounted on one thereof. With such a configuration, a user can insert the head into, for example, a pipe, and manipulate it to position the imaging head such that the target area is in its field of view. In a more preferred embodiment, the elongated member 14 is a telescoping boom as shown in FIG. 1.

In one embodiment, the positioning system comprises a targeting fixture 100 extending outwardly from the imaging head (see FIG. 6). The targeting fixture 100 comprises a distal end 100a which is biased outwardly from the head 27 such that, when pushed against a rigid surface, the distal end moves resiliently thereby effectively adjusting the position of the imaging head 15 relative to the surface. By gradually pushing down on the device 10, the imaging head 15 is lowered in a controlled way to reach the sweet spot. Once the sweet spot is found, the user holds the device 10 with the spring in the loaded position. It has been found that this provides an extremely reliable method of finding and maintaining the head in the sweet spot. In one embodiment, the distal end 100a comprises a bulbous portion 101 to increase its surface area in a direction normal to its biasing so that it does not penetrate, slip or shift upon the surface upon which it is placed. The distal end 100a may extend essentially parallel to the elongated member 14 or it may extend at an angle. For example, in some applications it may be useful to have distal end extend perpendicularly from the elongated member to allow the distal end to find purchase on a ledge or other structure element along a vertical pipe.

In one embodiment, the targeting fixture 100 comprises a bracket 104 effectively connected to the elongated member 14, a rod 103 having the distal end 100a and being slideably held by the bracket 104, and resilient means 107 for biasing the distal end away from bracket 104. The resilient means may be a spring (coil), electrometric material, or compressed fluid (such as air). In the embodiment shown in FIG. 6, the rod 103 comprises an outer tube 102a which is slideable through bracket 104 and which is fixed to a clamp 105. The outer tube 102a extends through the spring 107 and supports a flange 109. The spring 107 is thus captured between the bracket 104 and the flange 109. The inner rod 102b is slideable within the outer tube 102a and its distal end is biased away from the bracket 104 by the spring 107.

Alternative embodiments include air pistons such as the type used in closing doors.

The targeting fixture 100 is in one embodiment adjustable to allow for different sized pipes. That is, since the distance between the sweet spot and the wall of the pipe will change for different sized pipes, the position of the distal end will need to change too. In one embodiment, the targeting fixture is configured with a great deal of "stroke" in which the distal end 100a would extend outward a distance sufficient to accommodate the largest anticipated pipe and then be capable of being pushed inward to accommodate the smallest anticipated pipe. Alternatively, the targeting fixture may be adjustable in a coarse sense to approximate the diameter of the pipe and then be fine tuned by depressing resiliently the targeting fixture to realize the sweet spot.

With respect to this latter configuration, one embodiment is shown in FIG. 6 in which the rod 103 has calibration marking 108 corresponding to different diameter pipes. A clamp 105 is fixed to the outer tube 102a, and a clamp screw 106 is provided for securing to the inner rod 102b, thus capturing spring 107 and interconnecting outer tube 102a and inner rod 102b. This positions the distal end 100a in a predetermined relationship relative to the imaging head 15 while allowing repositioning of the distal end 100a within the range of travel permitted by the spring 107.

In operation, the user may preset the targeting fixture to the diameter of the lateral pipe by tightening the clamp 105 at the marking 108 corresponding to the pipe diameter—e.g., 8, 12, 15 and 18 inches. The markings are set so that the lamps 22, 23 will be slightly above the center of the pipe initially when the distal end is seated against the wall of the pipe. The user then pushes down on the device to advance the bracket 104, thereby loading the spring 107 by compressing it against flange 109, and lowering the head 27 until the sweet spot is found.

In one embodiment, the positioning system comprises an articulated mechanism 213 interposed between the enclosure of the imaging head and the boom to allow the imaging head to move relative to the boom. This articulated mechanism, in one embodiment, is a trunnion assembly 28 having an axis perpendicular to the axis of the boom as shown in FIG. 6. A simple trunnion is preferred because it provides for independent movement of the imaging device without incurring the cost, weight and complexity of a traditional pan and tilt mechanism, although such mechanisms are nevertheless within the scope of the invention.

In one embodiment, the imaging head is detachable from the positioning system to allow for its stationary operation. Such a configuration may be preferred, for example, in a surveillance application.

4. Identification System 215

The identification system 215 provides an indication of the location to which the recorded images pertain. The identification system may comprise a location recording system 216, which is in one embodiment an automated position locator such as a global position system, which provides the programmable controller with location data regarding the specific position of the imaging head. Such systems are well known. This information then can be automatically recorded along with image data. One can analogize the location data being recorded along with the image data to a date stamp on a photograph. The use of the location data, however, can be much more versatile and involve different graphical displays and output in combination with the image (see, e.g., the discussion above regarding step (d) of the inspection method).

The identification system 215 may also include correlating images with directional information. Such a feature is particularly beneficial if the GPS coordinates for a particular image are insufficient to identify the image. For example, it is not uncommon for several lateral pipes to terminate in a common manhole. Having just the GPS coordinates of the manhole therefore is insufficient to determine which lateral pipe is imaged. Accordingly, in one embodiment, the image is also correlated with information of the direction in which the image is taken (e.g., N, NE, E, SE, S, SW, W, NW, and N).

The identification system 215 may also comprise an indexing system 217 to catalog the images according to particular targets. Such systems are well known and described for example in U.S. Pat. No. 6,175,380.

5. Measurement System 214

The measuring system 214 functions to provide the user with target data from, for example, a target measurement device 219 or a range finder 218. For example, it may be preferable to employ the measurement system depicted and describe in U.S. Pat. No. 6,538,732 hereby incorporated by reference.

In another embodiment, the measurement system uses a laser range finder to determine the distance between the imaging head and the target object. In one embodiment, the range finder uses a beam to determine the distance to the object. In one embodiment, the beam is a laser beam, which produces a visual spot on the object, thereby providing visual confirmation to the operator of the point to which the beam is measuring. The object reflects the beam back to a photo-detector on the range finder where the reflected beam is detected. The time delay or wave phase difference between sending the beam and detecting the reflected beam is processed by circuitry within the range finder (e.g., a detector and time delay circuitry) to determine the distance between the range finder and the object. Alternatively, the range finder may incorporate sonic pulses or other conventional distance measuring technique. The range finder generates a measurement signal that corresponds to the distance between the range finder and the object. An example of a suitable range finder 106 is the DATA DISTO™ RS232 available through Leica AG, although other types of range finders will be readily apparent to those in the art.

In one embodiment, the laser of a range finder is adjustable in the same way lamps 23 are adjustable with respect to the embodiment of FIG. 8. To this end, the laser may be mounted on a mechanism similar to that of the lamp adjustment mechanism described above. In such an embodiment, the method may also comprise adjusting the range finder such that the laser beam is incident on the target while holding the imaging device essentially steady to image the target, While the present invention has been particularly shown and described with reference to the preferred mode as illustrated in the drawing, it will be understood by one skilled in the art that various changes in detail may be effected therein without departing from the spirit and scope of the invention as defined by the claims.

What is claimed is:

1. A method of inspecting a lateral pipe extending from a manhole, said method comprising:
   (a) inserting an imaging head into said manhole using a positioning system, said imaging head connected to an elongated member and comprising an imaging device adapted to convert an image to an image signal and having an optical axis, a lens optically coupled to said imaging device, and at least one lamp suitable for projecting a light beam, said lamp having a beam with a beam axis that is adjustable to enable said beam axis to move relative said optical axis;
   (b) imaging a target located within said lateral pipe;
   (c) holding said imaging device essentially steady while imaging said target and adjusting said beam to adjust the illumination of said target.

2. The method of claim 1, wherein said beam axis is adjusted to maximize the illumination of said target.

3. The method of claim 1, wherein said beam axis is adjusted by moving said lamp.

4. The method of claim 1, wherein said beam axis is adjusted by moving components of said lamp.

5. The method of claim 1, wherein said beam axis is adjusted automatically to maximize the luminance of said image.

6. The method of claim 1, wherein said beam axis is adjusted by said user using an operator control device.

7. The method of claim 1, wherein said beam axis moves in response to a zoom signal.

8. The method of claim 1, wherein said lamp moves such that said beam axis moves diagonally.

9. The method of claim 1, wherein said lamp comprises a plurality of lamps each having a beam axis that move together.

10. The method of claim 1, wherein said lamp comprises a plurality of lamps, each having a beam axis, wherein at least two of said plurality move differently.

11. The method of claim 10, wherein said at least two lamps move independently.

12. The method of claim 10, wherein moving said at least two lamps causes their beam axes to either converge or diverge.

13. The method of claim 1, wherein said imaging head also comprises an adjustable range finder having a laser beam to enable said laser beam to move independently of said imaging device, said method further comprising:
   (d) while holding said imaging device essentially steady to image said target, adjusting said range finder such that said laser beam is incident on said target.

14. An inspection system suitable for inspecting the interior of elongated structures, said system comprising:
   a positioning system comprising an elongated member;
   an imaging head connected to said elongated member and comprising an imaging device adapted to convert an image to an image signal and an optical axis, a lens optically coupled to said imaging device, and at least one lamp having an adjustable beam having a beam axis enabling said beam axis to move relative said optical axis; and
   an operator control device separate form said imaging head to control said imaging device.

15. The system of claim 14, wherein said lamp is mounted on a remote-controlled lamp adjustment mechanism that is connected to said imaging head, thereby enabling said lamp to move and said beam axis to move relative to said optical axis.

16. The system of claim 15, wherein said lamp adjustment mechanism is also controlled by a manual control on said operator's control device.

17. The system of claim 15, wherein said lamp adjustment mechanism is controlled automatically by one or more processors configured to determine the luminance of an image generated by said imaging device and to send a signal to actuate said lamp adjustment mechanism until luminance is maximized.

18. The system of claim 17, wherein said processors are configured to actuate said lamp automatically only after being initiated by a signal from said operator control device.

19. The system of claim 14, wherein said lamp comprises two spot lamps, each having a beam axis.

20. The system of claim 19, wherein each lamp has a lamp adjustment mechanism to enable each beam axis to move independently of each other.

21. The system of claim 19, wherein said lamps share a common lamp adjustment mechanism so that their beam axes move together.

22. The system of claim 21, wherein said lamp adjustment mechanism has one or more gears configured such that movement of said lamp adjustment mechanism results in different movement of said beam axes.

23. The system of claim 14, wherein said imaging head comprises a laser range finder to determine the distance between said imaging head and said target, said range finder having a laser beam that is adjustable relative to said imaging device.

24. A method of inspecting a pipe comprising:
   extending an imaging system into a manhole;
   imaging the interior of said manhole at a first magnification level of an imaging device;
   locating a lateral pipe connected to said manhole;
   imaging the interior of said lateral pipe at a second magnification level greater than said first level to image a target; and
   while holding the image of said target steady, adjusting a beam axis of a lamp on said imaging system to alter illumination of said target.

* * * * *